United States Patent [19]
Blackwell et al.

[11] Patent Number: 5,756,559
[45] Date of Patent: *May 26, 1998

[54] METHOD AND COMPOSITION FOR ADHERING TO TOOTH STRUCTURE

[75] Inventors: Gordon Blackwell, Constance, Germany; Chin-Teh Huang, Dover, Del.

[73] Assignee: Dentsply Research & Development, Milford, Del.

[*] Notice: The term of this patent shall not extend beyond the expiration date of Pat. No. 5,367,002.

[21] Appl. No.: 627,339

[22] Filed: Apr. 4, 1996

Related U.S. Application Data

[63] Continuation of Ser. No. 292,104, Aug. 22, 1994, abandoned, which is a continuation-in-part of Ser. No. 832,202, Feb. 6, 1992, Pat. No. 5,367,002.

[51] Int. Cl.⁶ .................................................. A61K 6/08
[52] U.S. Cl. ..................... 523/115; 524/116; 524/117; 524/118; 524/356
[58] Field of Search ........................... 523/115, 116, 523/117, 118; 524/356

[56] References Cited

U.S. PATENT DOCUMENTS

| | | | |
|---|---|---|---|
| 3,785,832 | 1/1974 | Bowen | 106/35 |
| 3,884,886 | 5/1975 | Pluddemann | |
| 4,107,845 | 8/1978 | Lee, Jr. et al. | 32/15 |
| 4,182,035 | 1/1980 | Yamauchi et al. | 433/228 |
| 4,499,251 | 2/1985 | Omura et al. | 526/278 |
| 4,514,342 | 4/1985 | Billington et al. | |
| 4,515,930 | 5/1985 | Omura et al. | 526/276 |
| 4,525,256 | 6/1985 | Martin | 204/159.18 |
| 4,537,940 | 8/1985 | Omura et al. | 526/278 |
| 4,540,722 | 9/1985 | Bunker | 523/109 |
| 4,544,467 | 10/1985 | Bunker et al. | 204/159.24 |
| 4,553,941 | 11/1985 | Aasen | 433/228.1 |
| 4,589,756 | 5/1986 | Saegusa | 354/432 |
| 4,593,054 | 6/1986 | Asmussen et al. | 523/118 |
| 4,636,533 | 1/1987 | Janda et al. | 522/14 |
| 4,640,936 | 2/1987 | Janda et al. | 522/14 |
| 4,645,456 | 2/1987 | James | 523/118 |
| 4,669,983 | 6/1987 | Bunker | 433/217.1 |
| 4,670,576 | 6/1987 | Bunker | 558/182 |
| 4,719,149 | 1/1988 | Aasen et al. | 428/473 |
| 4,816,495 | 3/1989 | Blackwell et al. | 522/14 |
| 4,855,475 | 8/1989 | Bunker | 558/182 |
| 4,863,993 | 9/1989 | Montgomery | 524/854 |
| 4,872,936 | 10/1989 | Engelbrecht | 156/307.3 |
| 4,880,660 | 11/1989 | Aasen et al. | 427/2 |
| 4,913,939 | 4/1990 | Montgomery | 427/389 |
| 4,929,746 | 5/1990 | Bunker | 558/92 |
| 4,945,006 | 7/1990 | Muggee et al. | 428/500 |
| 4,948,366 | 8/1990 | Horn et al. | 433/9 |
| 4,948,367 | 8/1990 | Haas | 433/9 |
| 4,966,934 | 10/1990 | Huang et al. | 524/315 |
| 5,064,495 | 11/1991 | Omura et al. | 156/307.3 |
| 5,085,726 | 2/1992 | Omura et al. | 156/307.3 |
| 5,089,051 | 2/1992 | Eppinger et al. | 106/35 |
| 5,091,441 | 2/1992 | Omura | 523/109 |
| 5,141,436 | 8/1992 | Orlowski | 433/226 |
| 5,177,121 | 1/1993 | Bunker | 523/116 |
| 5,186,783 | 2/1993 | Kawashima et al. | 156/307.3 |
| 5,218,070 | 6/1993 | Blackwell | 526/318 |
| 5,252,629 | 10/1993 | Imai et al. | 523/118 |
| 5,254,198 | 10/1993 | Kawashima et al. | 156/307.3 |
| 5,256,447 | 10/1993 | Oxman et al. | 427/207.1 |
| 5,264,513 | 11/1993 | Ikemura et al. | 526/318 |
| 5,295,824 | 3/1994 | Wong | 433/9 |
| 5,295,825 | 3/1994 | Betush | 433/28 |
| 5,304,585 | 4/1994 | Bunker | 523/116 |
| 5,356,951 | 10/1994 | Yearn et al. | 523/115 |
| 5,367,002 | 11/1994 | Huang et al. | 523/115 |

FOREIGN PATENT DOCUMENTS 0 323 120  7/1989  European Pat. Off.

OTHER PUBLICATIONS

Caulk, Technique Manual, Step–by–Step Procedures for the Cosmetic Repair of Dental Defects, Second Edition.
Caulk, Prisma APH, VLC Hybrid Composite.
Gunnar Ryge, vol. 30, No. 4, Clinical Criteria, pp. 347–358.
John F. Cvar and Gunnar Ryge, Clinical Evaluation of Dental Restorative Materials, U.S. Department of Health Education and Welfare, pp. 1, 10 and 11 and Appendix II.

*Primary Examiner*—Kriellion S. Morgan
*Attorney, Agent, or Firm*—Dale R. Lovercheck; James B. Bieber

[57] ABSTRACT

A composition and method of treating a dental tooth surface and adhering a restorative material to the treated dental tooth surface is provided. A liquid composition is applied to at least the portion of the tooth to form a treated surface. The composition includes at least 50 percent by weight of a volatile organic solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to dentin with a bond strength of at least 12 Mpa. Restorative material is then adhered to the treated surface with a bond strength of at least about 12 MPa.

47 Claims, No Drawings

METHOD AND COMPOSITION FOR ADHERING TO TOOTH STRUCTURE

This is a continuation of U.S. Ser. No. 08/292,104 filed Aug. 22, 1994, now abandoned, which is a continuation-in-part of U.S. Ser. No. 07/832,202 filed Feb. 6, 1992 (Case 1627) issued as U.S. Pat. No. 5,367,002 on Nov. 22, 1994.

The invention relates to adhesion of restoratives to teeth. The invention provides a method and composition for adhering to dental tooth surface. One or more portions of the composition are applied and cured on a cleaned tooth surface to form a treated tooth surface. A restorative material is applied to the tooth with a bond strength of at least about 12 MPa.

It is most desirable, when filling a tooth cavity with a filling material, such as a polymerizable dental restorative, to ensure good adhesion between the tooth surrounding the cavity and the set (polymerized) filling material since there is thereby obtained a good seal between the set filling material and the tooth which prevents, or at least markedly inhibits, ingress of mouth fluids and bacteria into the filled cavity and thus prevents further decay or loss of the filling material. In order to achieve good adhesion between the filler material and the tooth enamel, it has been recommended to provide a primer or adhesive bonding layer intermediate the filling material and surfaces of a prepared tooth. The prior art does not disclose a shelf stable single component composition adpated to bond polymerizable acrylate containing restoratives to dentin with a bond strength of at least 12 Mpa as is provided by the present invention.

Bowen in U.S. Pat. No. 3,785,832 discloses Dental Primer varnish. Pluddemann in U.S. Pat. No. 3,884,886 discloses Cationic Unsaturated Amine-Functional Silane Coupling Agents. Lee, Jr. et al in U.S. Pat. No. 4,107,845 discloses Dental Adhesive Composites. Yamauchi et al in U.S. Pat. No. 4,182,035 discloses Adhesive Compositions for the Hard Tissues of the Human Body. Omura et al. in U.S. Pat. No. 4,499,251 discloses Adhesive Compositions. Billington in U.S. Pat. No. 4,514,342 discloses Polyethylenically Unsaturated Monophosphates. Omura et al in U.S. Pat. No. 4,515,930 discloses Highly Water-Resistant Adhesive. Martin in U.S. Pat. No. 4,525,256 discloses Photopolymerizable Composition Including Catalyst Comprising Diketone Plus. Omura et al. in U.S. Pat. No. 4,537,940 discloses Adhesive Compositions. Bunker in U.S. Pat. No. 4,540,722 discloses Dentin and Enamel Adhesive. Bunker in U.S. Pat. No. 4,544,467 discloses Light-Curable Dentin ad Enamel Adhesive. Aasen in U.S. Pat. No. 4,553,941 discloses Acetal and Hemiacetal Dentin and Enamel Adhesive Primers. U.S. Pat. No. 4,589,756 relates to similar aromatic based compositions employed in dentistry. Asmussen et al. in U.S. Pat. No. 4,593,054 disclose Adhesion Promoting Agent, Process for its preparation and use thereof on Collageneous Material. Janda in U.S. Janda in U.S. Pat. No. 4,636,533 discloses Photopolymerizable Adhesion Promoting Dental Composition.

Janda in U.S. Pat. No. 4,640,936 discloses Photopolymerizable Phosphate-Containing Adhesive Promoting Dental Composition. James in U.S. Pat. No. 4,645,456 discloses Adhesive Composition for Tooth Enamel. Bunker in U.S. Pat. No. 4,669,983 discloses Dentin and Enamel Adhesive. Bunker in U.S. Pat. No. 4,670,576 discloses Polymerizable Phosphorus Esters. Aasen in U.S. Pat. No. 4,719,149 discloses Method for Priming Hard Tissue. Blackwell et al in U.S. Pat. No. 4,816,495 discloses Biologically Compatible Adhesive Visible Light Curable Compositions. Bunker in U.S. Pat. No. 4,855,475 discloses (Meth)Acrylic Esters of Phosphoric Acid Ester Dihalides. Montgomery in U.S. Pat. No. 4,863,993 discloses Surface Priming Composition for Proteinaceous Substrates; Method of Making and Using Same. Engelbrecht in U.S. Pat. No. 4,872,936 teaches dental cement mixtures containing polymerizable unsaturated monomers and/or oligomers and/or prepolymers containing acid groups and/or their reactive acid-derivative groups. Aasen et al in U.S. Pat. No. 4,880,660 discloses Method for Priming Hard Tissue. Montgomery in U.S. Pat. No. 4,913,939 discloses Method of Making and Using Surface Priming Composition for Proteinaceous Substrates. Bunker in U.S. Pat. No. 4,929,746 discloses Dentin and Enamel Adhesive. Muggee et al in U.S. Pat. No. 4,945,006 discloses Low Odor Adhesive Compositions and Bonding Method Employing Same. Horn et al in U.S. Pat. No. 4,948,366 discloses Adhesive Bond Strength Control for Orthodontic Brackets. Haas in U.S. Pat. No. 4,948,367 discloses Orthodontic Accessories and Method of Applying the Same. Huang et al in U.S. Pat. No. 4,966,934 discloses Biological Compatible Adhesive Containing a Phosphorous Adhesion Promoter and Accelerator. Omura et al in U.S. Pat. No. 5,064,495 discloses Method of Adhesion with a Mercapto Group Containing Adhesive. Omura et al in U.S. Pat. No. 5,085,726 discloses Method of Adhesion with a Sulfide Group Containing Adhesive. Eppinger et al in U.S. Pat. No. 5,089,051 discloses Adhesion-Promoting Dental Composition.

Omura in U.S. Pat. No. 5,091,441 discloses Dental Composition. Orlowski in U.S. Pat. No. 5,141,436 discloses Method of Bonding Article to Teeth Employing a Light Curable Primer. Bunker in U.S. Pat. No. 5,177,121 discloses Dentin and Enamel Adhesive. Kawashima et al. in U.S. Pat. No. 5,186,783 discloses Method of Bonding with Adhesive Composition Containing a Thiocarboxylic Acid Compound. Blackwell in U.S. Pat. No. 5,218,070 discloses Dental/Medical Composition and Use. Imai et al. in U.S. Pat. No. 5,252,629 discloses Adhesives for Dentin. Kawashima et al. in U.S. Pat. No. 5,254,198 discloses Method of Bonding a Metal or Alloy Utilizing a Polymerizable Thiocarboxylic Acid or a Derivative Thereof. Oxman et al. in U.S. Pat. No. 5,256,447 discloses Adhesive Composition and Method. Ikemura et al. in U.S. Pat. No. 5,264,513 discloses Primer Composition. Wong in U.S. Pat. No. 5,295,824 discloses Plastic Bracket with Adhesive Primer Layer and Methods of Making. Betush in U.S. Pat. No. 5,295,825 discloses Control System for Dental Handpieces. Bunker in U.S. Pat. No. 5,304,585 discloses Dentin and Enamel Adhesive.

Dental primers and adhesives in accordance with the invention have unexpectedly superior adhesion to dentin, enamel, cavity liner, bonding materials and filling materials.

It is an object of the invention to provide method of adhering a restorative material to a dental tooth by applying to the tooth a liquid composition comprising including at least 50 percent by weight of a volatile solvent, at least 15 percent by weight of one or more polymerizable acrylate compounds and an effective amount of a photoinitiator, at least a portion of the polymerizable compounds being multifunctional polymerizable compounds having at least three acrylate moieties, to form a polymeric material which adheres to dentin with a bond strength of at least 12 MPa.

It is an object of the invention to provide a method of adhering material to a tooth surface by sequentially including applying portions of a liquid priming/adhesive composition to a cleaned tooth surface and curing them to form a treated tooth surface.

It is an object of the invention to provide a restorative material bonded to the tooth with a bond strength of at least about 12 Mpa.

Volatile organic solvent(s) as used herein refers to organic solvent(s) which are substantially more volatile than water at 23° C.

"Acrylate" as used herein refers to unsaturated polymerizable compounds within the general formula:

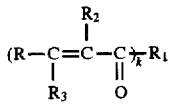

Wherein, k is an integer from 1 to 8,

R is hydrogen or methyl, $R_1$ is an alkyl having from 1 to 20 carbon atoms, $R_2$ is an alkyl having from 1 to 8 carbon atoms, and $R_3$ is an alkyl having from 1 to 12 carbon atoms.

"Polymerizable compound" as used herein refers to monomers and/or oligomers. Acrylates are preferred polymerizable compounds.

"Phosphates" as used herein does not include pyrophosphates.

Bond strength in units of MPa as used to herein in First and Second Comparatives Examples, Examples 1–10 and unless otherwise indicated refers to bond strength measured as follows: uncontaminated, caries free, extracted human teeth without significant anatomical alterations, defects or restorations were cleaned and disinfected by soaking in 1% sodium hypo chlorite solution for 18 to 24 hours, rinsed with water and are then stored at from 1 to 8 C. in 1% sodium chloride in water (saline solution) until used within six months. The wet teeth are then sanded flat by hand using wet 300 grit silicon carbide paper to expose an area of dentine at a plane just below the original interface between the enamel and the dentin, and this area of dentine is polished by hand with wet 600 grit silicon carbide paper. The teeth are kept wet in water until used within from 1 to 12 hours.

The dentine surface is dried lightly with a paper tissue, and the priming/adhesive solution of the invention applied in a thin layer using a dental operatory brush with bristles having a length of 5 mm and a diameter of 0.0025 inch. The solution is allowed to stand on the dentine surface for 10 seconds (unless otherwise noted) and the remaining solvent is evaporated by blowing the tooth gently with a stream of dry oil free air. The layer of primer/adhesive remaining is light cured by irradiating it for ten seconds (unless otherwise noted) with light from a dental light curing unit having a minimum output of 350 milliwatt/square centimeter in the 400 to 500 mm wavelength range (most preferably a Max lite, light curing unit, sold by Dentsply International, Inc., however in Examples 1 through 10 a Prismetics Lite, light curing unit, L.D. Caulk is used) . A portion of plastic straw of 5 mm internal diameter and about 4 mm long is placed end on to the prepared surface and filled with a light curing dental filling material (Dyract™, Dentrey Dentsply, Konstanz Germany unless otherwise noted). Finally the filling material is cured by irradiating with light from the dental light for forty seconds.

The prepared samples are stored for 24 hours in water at 37° C. before being thermocycled 500 times (unless otherwise noted) between 5° C. and 55° C. with a dwell time in each bath of 20 seconds. The thermocycled samples are left in water at 37° C. overnight before being tested in shear using a Zwick universal testing machine model 145501 with the load cell set for a maximum load of 500 Newtons, and operating at a crosshead speed of 1 mm per minute using a 2 mm diameter cylindrical chisel. The chisel has a tip point formed at the lower end by grinding and polishing a planar surface across the end of the cylinder at a 45 degree angle to the central axis of the cylinder. The tip point is formed at the intersection of a planar surface with the lower end of the chisel. In test position the tip point of the chisel is applied against the composite. Each tooth is vertically mounted in plastic for the test.

SUMMARY OF THE INVENTION

A method of adhering a restorative material to a dental tooth by applying a liquid composition to at least a portion of said tooth to form a treated surface. The composition includes at least 50 percent by weight of a volatile organic solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which adheres to dentin with a bond strength of at least 12 MPa. Restorative material is then affixed to at least a portion of the treated surface with a bond strength of at least about 12 MPa.

DETAILED DESCRIPTION OF THE INVENTION

A method of conditioning a tooth surface including applying a first portion of a liquid priming adhesive composition to a cleaned tooth surface and curing the first portion of liquid primer adhesive composition to form a primed tooth surface. Then a second portion of the liquid priming adhesive composition is applied to the primed tooth surface and cured to form a conditioned tooth surface. A polymerizable restorative composition is bonded to the tooth with a bond strength of at least about 12 MPa. Priming adhesive compositions useful in accordance with the invention preferably include in order of increasing preference at least 50, 60, 70 or 80 percent by weight of a volitile solvent and at least 15 percent by weight of a polymerizable compound.

In accordance with a preferred embodiment of the invention is provided a method of adhering a restorative material to a dental tooth by applying a dental composition which includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which adheres to dentin with a bond strength of at least 12 MPa.

Preferably the composition includes in order of increasing preference at least 2, 2.5, 3, 3.5, 4, 5, 6, or 7 percent by weight of the multifunctional polymerizable compounds. Preferably the solvent is dimethyl ketone or methyl ethyl ketone and the bond strength is at least 15 MPa. Preferably the composition comprises at least 75 percent by weight of said solvent. Preferably at least a portion of the multifunctional polymerizable compounds are phosphate esters.

Preferably at least a portion of the multifunctional compounds have a chemical structure within the scope of the general formula:

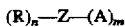

wherein each R independently is an acrylate containing moiety, Z is an organic moiety, each A is independently is a phosphate, n is an integer greater than 2, m is an integer of 1 or more. Preferably at least a portion of the polymerizable compounds are acids and the acids comprise at least 2 percent by weight of the composition. Preferably at least a portion of the polymerizable compounds are acid esters.

In accordance with a preferred embodiment of the invention is provided a method of treating a dental tooth by applying a first portion of a liquid composition to a dental tooth surface. The polymerizable compounds in the first portion of the liquid composition are cured (polymerized) to form a primed tooth surface.

In accordance with a preferred embodiment of the invention is provided a method of adhering a restorative material to a dental tooth by applying a liquid composition to at least a portion of the tooth to form a treated surface. The composition includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to dentin with a bond strength of at least 12 Mpa. Restorative material is then affixed to at least a portion of the treated surface with a bond strength of at least about 12 MPa.

Acid-etching of enamel may be done but is not necessary. To fill deep tooth cavities it is preferred to cover the dentine closest to the pulp of the tooth with a hard-setting calcium hydroxide liner (such as DYCAL, sold by Dentsply International Inc.) leaving the rest of the cavity floor and walls free for chemical bonding with a dental restorative such as Dyract, sold by Dentsply International Inc.

Preferred volatile solvents include, ethanol, methanol, isopropanol, dimethyl ketone, ethylmethyl ketone, and mixture of these.

Preferred monomers for use in primer adhesive compositions in accordance with the inventor have a solubility in water of less than about 5%, and more preferably have a solubility in water of less than 1%. Exemplary monomers include triethylene glycol dimethacrylate, tetraethyleneglycol dimethacrylate, glycerol-1,2-dimethacrylate, glycerol-1, 3-dimethacrylate, the reaction product of butanediol diglycidyl ester and methacrylic acid, tetrahydrofurfural methacrylate, methacryloxyethyl maleic ester, methacryloxyethyl succinate, urethane dimethacrylate, Bis-GMA, Ethoxylated bisphenol-A dimethacrylate, bisphenol-A dimethacrylate, and mixtures thereof. Monomers having a solubility in water higher than 5% are less preferred. Monomer having a solubility in water less than about 1% are more preferred. Highly water soluble monomers such as hydroxyethyl methacrylate and hydroxypropyl methacrylate tend to provide lower adhesion and are less suitable for use in compositions of the invention.

A volatile solvent is removed after application of the primer of the dentine surface. The monomer is preferably less volatile than the solvent.

In use, compositions of the invention are applied to a clean dry dentine surface, and the solvent is evaporated, for example, by application of a gentle stream of air. The layer of resin remaining is preferably cured by exposing it to light from a dental curing lamp. The composite filler formation is then applied by exposing it to light from a dental curing lamp and cured.

Prior art dentine adhesive systems giving adhesion higher than 12 MPa have required separate applications of a primer composition and an adhesive composition. The combined primer/adhesive composition of the present invention achieves high bond strength adhesion levels with application of one liquid.

As the free radical-polymerizable monomer or prepolymer to be employed in this invention, use may be made of any monomer, dimer, trimer, or other oligomer of the type that is usable in dental applications. Thus, the polymerizable monomer portion of the present adhesive composition generally comprises one or more monofunctional or polyfunctional ethylenically unsaturated monomers or prepolymers, e.g., dimers, trimers, and other oligomers, or mixtures or copolymers thereof, based on acrylic or methacrylic or itaconic acid, or derivatives thereof, including their esters which can be polymerized by free radical initiation. These materials include, but are not limited to acrylic and methacrylic acid, itaconic acid and the like, acrylic or methacrylic or itaconic acid esters of monohydric or polyhydric alkanols or polyhydric alcohols containing at least one phenyl group. Examples of such compound include monovinylmethacrylates, e.g., methylmethacrylate, ethyl acrylate, propyl methacrylate, hydroxyethylmethyacrylate, hydroxypropylmethacrylate, diethylene glycol acrylate, triethylene glycol acrylate, the monoester of trimellitic acid with hydroxyethyl methacrylate, hydroxypropyl itaconate and the like, esters of aliphatic polyhydric alcohols, such as for example, the di- and polyacrylates, the di- and polymethacrylates, and the di- and polyitaconates of alkylene glycols, alkoxylene glycols, alicyclic glycols and higher polyols, such as ethylene glycol, triethylene glycol, tetraethylene glycol, tetramethylene glycol, trimethylolethane, trimethylolpropane, pentaerythritol, dipentaerythritol, tripentaerythritol, and the like, or mixtures of these with each other or with their partially esterified analogs, and their prepolymers, such compound or mixture optionally having free hydroxyl content. Typical compounds of this type, include but are not limited to, trimethylolpropane triacrylate, trimethylolethane triacrylate, trimethylolpropane trimethacrylate, trimethylolethane trimethacrylate, tetramethylene glycol dimethacrylate, ethylene glycol dimethacrylate, triethylene glycol dimethacrylate, tetraethylene glycol diacrylate, tetraethylene glycol dimethacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexacrylate, tripentaerythritol octaacrylate, pentaerythritol dimethacrylate, pentaerythritol trimethacrylate, dipentaerythritol dimethacrylate, glycerin trimethacrylate, ethylene glycol dimethacrylate, butanediol dimethacrylate, trimethylolpropane trimethacrylate, tetramethylolmethane tetramethacrylate, bisphenol-A dimethacrylate, bisphenol-A diglycidyl methacrylate, 2,2,'-bis-(4-methacryloxyethoxyphenyl) propane and so on.

Also included among the polymerizable monomers which may be used are the vinyl urethane or urethane-acrylate prepolymers which are well known in the art. These prepolymers are polymerizable by free radical initiation and may be prepared, for example, by reacting an organic diisocyanate or an isocyanate-terminated urethane prepolymer with an ethylenically unsaturated monomer which is reactive with the diisocyanate or urethane prepolymer. These polymers also may be prepared by reacting a hydroxyl-containing material, such as a polyol or a hydroxyl-terminated urethane prepolymer with an ethylenically unsaturated monomer which is reactive with the polyol or hydroxyl-terminated urethane. The urethane prepolymers, which may be linear or branched, carry isocyanate end groups and generally are prepared by reacting a compound having hydroxyl functionality with a molar excess of diisocyanate.

Any of a wide variety of diisocyanates may be used to prepare the isocyanate-terminated urethane prepolymer including aliphatic, cycloaliphatic, heterocyclic, and aromatic diisocyanates, and combinations of these. Examples include, but are not limited to, 2,4-tolylene diisocyanate, 2,6-tolylene diisocyanate, 1,4-phenylene diisocyanate, 2,2,4-trimethyl hexamethylene diisocyanate, hexamethylene diisocyanate, 1,4-naphthalene diisocyanate, 1,5-naphthalene diisocyanate, 4,4,'-diphenylmethane diisocyanate, p,p,'-diphenyl diisocyanate, butylene-1,4-diisocyanate, ethylene diisocyanate, trimethylene diisocyanate, tetramethylene-1,4-diisocyanate, butylene-2,3-diisocyanate, cyclohexylene-1,2-diisocyanate, methylene-bis-(4-phenyl-isocyanate), diphenyl-3,3,'-dimethyl-4,4,'-diisocyanate, xylylene diisocyanate, cyclohexane-1,4-diisocyanate, 1-methoxyphenyl-2,4-diisocyanate and the like, and mixtures thereof.

A wide variety of compounds having hydroxyl functionality may be used to form the isocyanate-terminated urethane prepolymers. For example, diols of the structure

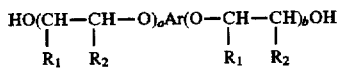

may be used, where R1 and R2 are hydrogen atoms or alkyl groups, e.g., methyl, and Ar is a divalent aromatic group in which each free valency is on an aromatic carbon atom, and where a and b, independently, may be zero or an integer. Other suitable hydroxyl containing compounds include diols and polyols such as ethylene glycol, propylene glycol, triethylene glycol, tetramethylene glycol, trimethylolpropane, pentaerythritol, dipentaerythritol, and the like, or esters of acrylic acid, methacrylic acid or itaconic acid or the like with aliphatic polyhydric alcohols. Among the more preferred hydroxyl containing compounds are the esters of acrylic or methacrylic acid and a hydroxyalkanol of at least two carbon atoms such as hydroxyethyl acrylate, hydroxyethyl methacrylate, hydroxypropyl acrylate, hydroxypropyl methacrylate, hydroxyisopropyl methacrylate, and the like.

Formation of the isocyanate terminated urethane prepolymers may be assisted by the use of a catalyst known in the art to assist polyurethane formation, for example, tertiary amines and metal salts, e.g., tin salts, titanium salts and the like.

To form the vinyl urethane or urethane-acrylate prepolymer starting materials, an isocyanate-terminated urethane prepolymer or a diisocyanate is reacted with an ethylenically unsaturated compound having hydroxyl functionality. These compounds include for example, esters of acrylic acid, methacrylic acid or itaconic acid with aliphatic polyhydric alcohols, such as hydroxyethyl acrylate, hydroxypropyl methacrylate or the like. The resulting vinyl urethanes are well known in the art and are described for example, in U.S. Pat. No. 3,629,187 to Waller, U.S. Pat. No. 3,759,809 to Carlick et al, U.S. Pat. No. 3,709,866 to Waller and U.S. Pat. No. 4,459,193 to Ratcliffe et al, and all of these patents are incorporated herein by reference.

Formation of the vinyl urethane prepolymers may be assisted by the use of the same catalysts noted above, namely, tertiary amines and metal salts.

The foregoing list of polymerizable ethylenically unsaturated monomers and prepolymers is intended to be exemplary only, and other known polymerizable materials can be used in compositions of this invention.

In accordance with a preferred embodiment of the invention two or more ethylenically unsaturated compounds are included in dental treatment compositions. In a preferred embodiment of the invention the polymerizable monomer is liquid at temperatures from about 20° C. to about 25° C.

Preferred monomers are TEGDMA, glyceryl dimethacrylate, polyethylene glycol dimethacrylate, trimethylolpropane, trimethacrylate, UDMA, R5-62-1, EBPDMA, and ethylene glycol dimethacrylate.

Preferred solvents are ethanol, 2-propanol, and dimethyl ketone.

A preferred bonding composition in accordance with a preferred embodiment of the invention includes 10 percent by weight of ENTA; 10 percent by weight of urethane diacrylate; 2.5 percent by weight of TEGDMA; 0 to about 1 percent by weight of glutaraldehyde; 0.2 percent by weight of CQ; 0.4 percent by weight of EDAB; 0.1 percent by weight of BHT; from 80.8 to about 81.8 percent by weight of dimethyl ketone.

A preferred etchant includes 10 percent by weight of $H_3PO_4$; 2.5 percent by weight of $AlCl_3$; 87.5 percent by weight of water.

Exemplary acrylic monomers for use in compositions of the invention include: 1,4-butanediol dimethacrylate (BDEM); glyceryl dimethacrylate (GlyDM); hydroxyethyl methacrylate (HEMA); triethyleneglycol dimethacrylate (TGD); tetrahydrofuran dimethacrylate (THFMA).

Having generally described the invention, a more complete understanding can be obtained with reference to certain specific examples, which are included for purposes of illustration only. It should be understood that the invention is not limited to the specific details of the Examples.

FIRST COMPARATIVE EXAMPLE

A commercially available primer composition is made by stirring 6 percent by weight of PENTA, 30 percent by weight of HEMA, 63.9 percent by weight of 95% ethanol; and 0.1 percent by weight of BHT. The primer composition is applied to a cleaned tooth surface, cured and then Dyract, a polymerizable acrylate containing restorative is applied which forms a bond strength of 6.3 MPa.

SECOND COMPARATIVE EXAMPLE

The procedure of the First Comparative Example is followed except that after curing the primer composition, a commercially available adhesive composition is applied and cured. The adhesive composition is made by stirring 24.90 percent by weight of triethylene glycol dimethacrylate, 9.24 percent by weight of bisphenol-A-dimethacrylate, 0.03 percent by weight of butylated hydroxy toluene, 2.0 percent by weight of morpholino ethyl methacrylate, 0.12 percent by weight of lithium P-toluenesulfinate, 0.24 percent by weight of camphorquinone, 53.32 percent by weight of urethane diacrylate, 4.55 percent by weight of DPEPAP, and 5.6 percent by weight of HEMA. The restorative forms a bond having bond strength of 10 MPa.

EXAMPLE 1

A) Priming Adhesive Composition

A priming and adhesive polymerizable composition in accordance with the invention is formed by stirring 10.00 grams of 7,7,9,63,65 hexamethyl-4,13,60,69-tetra-oxo-3,14,19,24,29,34,39,44,49,54,59,70-dodecanaoxa-5,12,61,68-tetra-azadoheptacontane-1,72 diyl-dimethacrylate, (also known as urethane dimethacrylate resin); 5.00 grams of 2,2,6-6 tetra acryloxyloxymethyl-4, 8 dioxa-9-oxo-11-undecyl phosphoric acid, also known as dipentaerythritol pentacrylate phosphoric acid ester (PENTA); 5.00 grams of 2-propenoic acid, 1-methyl-1, 2-ethanediyl-bis (oxy-21-ethanediyl)ester; also known as triethylene glycol dimethacrylate (TEGMA); 0.01 grams of phenol, 2,6-bis-(1,1-dimethethyl-4-methyl), also known as butylated hydroxytoluene (BHT); 0.020 grams of bicyclo [2.2.1] heptane-2, 3-dione 1,7,7-trimethyl, also known as camphorquinone; 0.60 grams of 4-Ethyl dimethyl aminobenzoate (DMABE), and 79.19 grams of dimethyl ketone also known as dimethyl ketone.

B) Priming a tooth surface

A dental tooth surface of dentine and enamel is cleaned with pumice. Then the tooth surface is washed thoroughly with water spray and air-dried. Three drops of the priming adhesive composition, made by following the procedure of Example 1 Section A, are applied directly onto a brush. The priming adhesive composition is applied to the cleaned tooth surface with the brush to thoroughly wet the exposed dentine and enamel surface. The surface is left undisturbed for 30 seconds. Excess solvent is removed by blowing with air from a dental syringe. The priming adhesive composition is then cured for 10 seconds to form a priming adhesive treated tooth.

C) Applying restorative

Immediately Dyract restorative, sold by Dentsply International Inc. is placed over the cured priming adhesive. The restorative bonds to the treated tooth surface with a bond strength of 14.4 MPa.

EXAMPLE 2

A) A primer adhesive composition is formed by stirring 81.56 grams of dimethyl ketone, 5.0 grams of triethyleneglycol dimethacrylate (TGD), 10.0 grams of urethane diacrylate, 2.5 grams of PENTA, 0.20 grams of camphorquinone, 0.60 grams of DMABE, 0.05 grams of butylated hydroxytoluene (BHT).

B) The procedure of Example 1, sections B and C is followed except that the composition of Example 2 section A is used in place of the composition of Example 1, section A to form a restorative bonded to tooth dentin having a bond strength of 13.4 MPa.

EXAMPLE 3

A) A primer adhesive composition is formed by stirring 76.65 grams of dimethyl ketone, 5.0 grams of TGD, 10.0 grams of urethane diacrylate, 7.5 grams of PENTA, 0.20 grams of camphorquinone, 0.60 grams of DMABE, 0.05 grams of BHT.

B) The procedure of Example 1, sections B and C is followed except that the composition of Example 3 section A is used in place of the composition of Example 1, section A to form a restorative bonded to the tooth dentin having a bond strength of 16.0 MPa.

EXAMPLE 4

A) A primer adhesive composition is formed by stirring 71.65 grams of dimethyl ketone, 5.0 grams of TGD, 10.0 grams of urethane diacrylate, 12.5 grams of PENTA, 0.20 grams of camphorquinone, 0.60 grams of DMABE, 0.05 grams of BHT.

B) The procedure of Example 1, sections B and C is followed except that the composition of Example 4 section A is used in place of the composition of Example 1, section A to form a restorative bonded to the tooth dentin having a bond strength of 15.5 MPa.

EXAMPLE 5

A) A primer adhesive composition is formed by stirring 81.65 grams of dimethyl ketone, 7.5 grams of TGD, 7.5 grams of urethane diacrylate, 2.5 grams of PENTA, 0.20 grams of camphorquinone, 0.60 grams of DMABE, 0.05 grams of BHT.

B) The procedure of Example 1, sections B and C is followed except that the composition of Example 5 section A is used in place of the composition of Example 1, section A to form a restorative bonded to the tooth dentin having a bond strength of 12.5 MPa.

EXAMPLE 6

A) A primer adhesive composition is formed by stirring 79.15 grams of dimethyl ketone, urethane diacrylate, 15.0 grams of urethane dimethacrylate, 5.0 grams of PENTA, 0.20 grams of camphorquinone, 0.60 grams of DMABE, 0.05 grams of BHT.

B) The procedure of Example 1, sections B and C is followed except that the composition of Example 6 section A is used in place of the composition of Example 1, section A to form a restorative bonded to the tooth dentin having a bond strength of 13.9 MPa.

EXAMPLE 7

A) A primer adhesive composition is formed by stirring 80 grams of ethanol, 15 grams of TGD, 5 grams of PENTA, 0.20 grams of camphorquinone, 0.60 grams of DMABE, 0.05 grams of BHT.

B) The procedure of Example 1, sections B and C is followed except that the composition of Example 7 section A is used in place of the composition of Example 1, section A to form a restorative bonded to the tooth dentin having a bond strength of 12.7 MPa.

EXAMPLE 8

A) A primer adhesive composition is formed by stirring 60 grams of ethanol, 35 grams of triethyleneglycol dimethacrylate (TGD), 5.0 grams of PENTA, 0.20 grams of camphorquinone, 0.60 grams of DMABE, 0.05 grams of BHT.

B) The procedure of Example 1, sections B and C is followed except that the composition of Example 8 section A is used in place of the composition of Example 1, section A to form a restorative bonded to the tooth dentin having a bond strength of 12 MPa.

EXAMPLE 9

A) A primer adhesive composition is formed by stirring 80 grams of ethanol, 15 grams of tetrahydrofaran dimethacrylate (THFMA), 5 grams of PENTA, 0.20 grams of camphorquinone, 0.60 grams of DMABE, 0.05 grams of BHT.

B) The procedure of Examples 1, sections B and C is followed except that the composition of Example 9 section A is used in place of the composition of Example 1, section A to form a restorative bonded to the tooth dentin having a bond strength of 12.6 MPa.

EXAMPLE 10

A) A primer adhesive composition is formed by stirring 80 grams of dimethyl ketone, 5 grams of TGD, 10 grams of urethane diacrylate, 5 grams of PENTA, 0.20 grams of camphorquinone, 0.60 grams of DMABE, 0.05 grams of BHT.

B) The procedure of Example 1, sections B and C is followed except that the composition of Example 10 section A is used in place of the composition of Example 1, section A to form a restorative bonded to the tooth dentin having a bond strength of 14.4 MPa.

EXAMPLE 11

A tooth dentine is etched. A liquid composition is prepared by stirring 6 grams of PENTA, 12 grams of TCB, 0.2 grams of CQ, 0.4 grams ethyl 4-dimethylaminobenzoate (DMABE), 0.05 grams of BHT and 87.35 grams of 95% ethanol. The liquid composition is applied onto the tooth by brushing. Then Prisma® APH™ restorative (sold by Dentsply International Inc.) is applied to the tooth and cured to obtain a bond having a bond strength of 22.6 MPa.

For Example 11 shear bond strength is determined by treating extracted human teeth in 1% sodium hypochlorite for 18 to 24 hours, washing with water, and storing in distilled water in a refrigerator at about 4° C. until needed. The teeth are mechanically wet sanded with 120/320/600 grit carborundum paper until the dentin is exposed. Each tooth sample is then prepared by blotting dry exposed dentin with absorbent material, such as Kimwipe; etching dentin with 10% phosphoric acid for 15 seconds; rinsing with water for 15 seconds; and then blotting dry with absorbent material, such as Kimwipe. Two coats of adhesive composition are then applied to dentin with a brush for 30 seconds; dried with oil-free air for five seconds; curing for 20 seconds with a Max™Lite light curing unit. Prisma®APH™ restorative is placed in a cylindrical plastic matrix with a 3.68 mm inside diameter, set on the treated dentin and cured for 40 seconds. The specimens are stored in distilled water for approximately 24 hours at 37° C. Each specimen is mounted vertically in a plastic cylinder with self cure polymethyl methacrylate so that the dentin surface is parallel to the Instron needle; and then debonded on an Universal Instron with a crosshead speed of 5 mm/minute. The bond strength is then calculated in MPa.

While present embodiments of the invention and methods of practicing the same have been illustrated and described, it will be recognized by those skilled in the art that this invention may be otherwise variously embodied and practiced within the scope of the following claims.

What is claimed is:

1. A dental composition, comprising:
    at least 50 percent by weight of a volatile organic solvent, at least 15 percent by weight of one or more polymerizable acrylate compounds and an effective amount of a photoinitiator, at least a portion of said polymerizable compounds are multifunctional polymerizable compounds having at least three acrylate moieties and a phosphate moiety, said polymerizable compound being substantially soluble in said solvent, said compositions being adapted to form a polymeric material which adheres to dentin with a bond strength of at least 12 MPa.

2. The composition of claim 1 wherein said composition comprises at least 2 percent by weight of said multifunctional polymerizable compounds.

3. The composition of claim 1 wherein said composition comprises at least 2.5 percent by weight of said multifunctional polymerizable compounds.

4. The composition of claim 1 wherein said composition comprises at least 3 percent by weight of said multifunctional polymerizable compounds.

5. The composition of claim 1 wherein said composition comprises at least 3.5 percent by weight of said multifunctional polymerizable compounds.

6. The composition of claim 1 wherein said composition comprises at least 4 percent by weight of said multifunctional polymerizable compounds.

7. The composition of claim 1 wherein said composition comprises at least 5 percent by weight of said multifunctional polymerizable compounds.

8. The composition of claim 1 wherein said composition comprises at least 6 percent by weight of said multifunctional polymerizable compounds.

9. The composition of claim 1 wherein said composition comprises at least 7 percent by weight of said multifunctional polymerizable compounds.

10. The composition of claim 1 wherein said solvent is dimethyl ketone or methyl ethyl ketone and said bond strength is at least 15 MPa.

11. The composition of claim 1 wherein said composition comprises at least 75 percent by weight of said solvent.

12. The composition of claim 2 wherein at least a portion of said multifunctional polymerizable compounds are phosphate esters.

13. The composition of claim 4 wherein said solvent is dimethyl ketone and said bond strength is at least 15 MPa.

14. The composition of claim 1 wherein at least a portion of said polymerizable compounds are acids and said acids comprise at least 2 percent by weight of said composition.

15. The composition of claim 14 wherein said composition further comprises a polymerizable compound having at least two acrylate moieties and a gram molecular weight greater than 200, said polymerizable compound being adapted to form an elastomer when polymerized.

16. The composition of claim 14 further comprising carboxylic acids.

17. The composition of claim 1 wherein at least a portion of said polymerizable compounds are acid esters.

18. A method of treating a dental tooth, comprising:
    applying a first portion of a liquid composition to a dental tooth surface, said liquid composition comprising at least 50 percent by weight of a volatile organic solvent, at least 15 percent by weight of one or more polymerizable acrylate compounds and an effective amount of a photoinitiator, at least a portion of said polymerizable compounds are multifunctional polymerizable compounds having at least three acrylate moieties and a phosphate moiety, said polymerizable compound being substantially soluble in said solvent, said compositions being adapted to form a polymeric material which adheres to dentin with a bond strength of at least 12 MPa and curing said polymerizable compounds in said first portion of said liquid composition to form a primed tooth surface.

19. The method of claim 18 further comprising applying a second portion of said liquid composition to said primed tooth surface,
    and curing said polymerizable compound in said second portion of said liquid priming adhesive composition to form a conditioned tooth surface.

20. The method of claim 18 further comprising applying a polymerizable restorative composition to said conditioned tooth surface.

21. The method of claim 18 further comprising curing said polymerizable restorative composition to form a polymeric restorative bonded to said tooth with a bond strength at least 15 MPa.

22. The method of claim 18 wherein said composition further comprises at least 20 percent by weight of a volatile solvent.

23. The method of claim 18 wherein said composition comprises at least 3 percent by weight of said multifunctional polymerizable compounds.

24. The method of claim 18 wherein said composition comprises at least 4 percent by weight of said multifunctional polymerizable compounds.

25. The method of claim 18 wherein said composition comprises at least 5 percent by weight of said multifunctional polymerizable compounds.

26. The method of claim 18 wherein said composition further comprises a polymerization initiator.

27. The method of claim 18 further comprising curing said polymerizable restorative composition to form a polymeric restorative bonded to said tooth with a bond strength at least 15 MPa.

28. A method of adhering a restorative material to a dental tooth, comprising:

applying a liquid composition to at least a portion of said tooth to form a treated surface, said composition comprising at least 50 percent by weight of a volatile organic solvent, at least 15 percent by weight of one or more polymerizable acrylate compounds and an effective amount of a photoinitiator, at least a portion of said polymerizable compounds are multifunctional polymerizable compounds having at least three acrylate moieties and a phosphate moiety, said polymerizable compounds being substantially soluble in said solvent, said composition being adapted to form a polymeric material which is adapted to adhere to dentin with a bond strength of at least 12 MPa and affixing restorative material to at least a portion of said treated surface with a bond strength of at least about 12 MPa.

29. The method of claim 28 wherein said material is a polymerizable composite filling material.

30. The method of claim 28 wherein said bond strength is 16 MPa.

31. The method of claim 28 wherein said composition comprises of at least 75 percent by weight of a volatile solvent.

32. The method of claim 28 wherein said dental tooth material is an enamel.

33. The method of claim 28 wherein said composition comprises at least 3 percent by weight of said multifunctional polymerizable compounds.

34. The method of claim 28 wherein said composition comprises at least 4 percent by weight of said multifunctional polymerizable compounds.

35. The method of claim 28 wherein said composition comprises at least 5 percent by weight of said multifunctional polymerizable compounds.

36. A polymeric material adhered to dentin and polymeric restorative formed from a polymerizable restorative composition, said polymeric material being formed from a dental composition comprising at least 50 percent by weight of a volatile organic solvent, at least 15 percent by weight of one or more polymerizable acrylate compounds and an effective amount of a photoinitiator, at least a portion of said polymerizable compounds being multifunctional polymerizable compounds having at least three acrylate moieties and a phosphate moiety, said polymerizable compound being substantially soluble in said solvent, said dental composition forming said polymeric material adhered to dentin and said polymeric restorative with a bond strength of at least 12 MPa.

37. The dental composition of claim 36 wherein said dental composition comprises at least 5 percent by weight of said multifunctional polymerizable compounds.

38. The dental composition of claim 36 wherein said dental composition comprises at least 6 percent by weight of said multifunctional polymerizable compounds.

39. The dental composition of claim 36 wherein said dental composition comprises at least 7 percent by weight of said multifunctional polymerizable compounds.

40. The dental composition of claim 36 wherein said solvent is dimethyl ketone or methyl ethyl ketone and said bond strength is at least 15 MPa.

41. The dental composition of claim 36 wherein said dental composition comprises at least 75 percent by weight of said solvent.

42. The dental composition of claim 36 wherein at least a portion of said multifunctional polymerizable compounds are phosphate esters.

43. The dental composition of claim 36 wherein said solvent is dimethyl ketone and said bond strength is at least 15 MPa.

44. The dental composition of claim 36 wherein at least a portion of said polymerizable compounds are acids and said acids comprise at least 2 percent by weight of said composition.

45. The dental composition of claim 36 wherein said composition further comprises a polymerizable compound having at least two acrylate moieties and a gram molecular weight greater than 200, said polymerizable compound being adapted to form an elastomer when polymerized.

46. The dental composition of claim 36 further comprising carboxylic acids.

47. The dental composition of claim 45 wherein at least a portion of said polymerizable compounds are acid esters.

\* \* \* \* \*